United States Patent
Lind

(10) Patent No.: US 8,337,453 B2
(45) Date of Patent: Dec. 25, 2012

(54) DRUG PELLET MOLDING ONTO PLUNGER ASSEMBLY

(75) Inventor: Casey Jean Lind, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 248 days.

(21) Appl. No.: 12/327,020

(22) Filed: Dec. 3, 2008

(65) Prior Publication Data

US 2010/0137785 A1 Jun. 3, 2010

(51) Int. Cl.
*A61M 5/31* (2006.01)
(52) U.S. Cl. ............ 604/60; 604/59; 604/124; 604/187; 604/218
(58) Field of Classification Search .............. 604/57–60, 604/82–92, 124, 141, 144, 149, 152, 184, 604/187, 196, 218, 228, 229–230, 235
See application file for complete search history.

(56) References Cited

U.S. PATENT DOCUMENTS

| | | | | |
|---|---|---|---|---|
| 3,424,158 A * | 1/1969 | Silver | ............................ | 604/514 |
| 3,934,584 A * | 1/1976 | Corio | ............................ | 604/59 |
| 4,020,974 A * | 5/1977 | Bauer et al. | .................... | 221/307 |
| 4,357,136 A * | 11/1982 | Herskovitz et al. | ............ | 433/224 |
| 6,991,457 B2 * | 1/2006 | Kazen et al. | .................... | 433/32 |
| 2007/0270744 A1 * | 11/2007 | Dacquay et al. | .............. | 604/114 |

* cited by examiner

*Primary Examiner* — Quynh-Nhu H Vu
(74) *Attorney, Agent, or Firm* — Kenneth D. Bassinger

(57) ABSTRACT

A pellet loading apparatus has a pellet housing configured to receive and hold a plunger so that a cavity is formed by an interior surface of the pellet housing and the plunger. A pellet is located or formed in the cavity. A dispensing chamber housing is located in a disposable drug delivery device. The dispensing chamber housing is configured to couple with the pellet housing so that the plunger and the pellet can be loaded into the dispensing chamber housing.

5 Claims, 4 Drawing Sheets

DRUG PELLET MOLDING ONTO PLUNGER ASSEMBLY

BACKGROUND OF THE INVENTION

The present invention relates to molding drug pellets for an injection device and more particularly to a molding apparatus for a drug suspended in a phase transition compound.

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

These, and other diseases, can be treated by injecting a drug into the eye. Such injections are typically done manually using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 causes the plunger 120 to expel the drug through needle 105.

In using such a syringe, the surgeon is required to pierce the eye tissue with the needle, hold the syringe steady, and actuate the syringe plunger (with or without the help of a nurse) to inject the fluid into the eye. Fluid flow rates are uncontrolled. The volume injected is typically not controlled in an accurate manner because reading the vernier is subject to parallax error. Tissue damage may occur due to an "unsteady" injection.

An effort has been made to control the delivery of small amounts of liquids. A commercially available fluid dispenser is the ULTRA™ positive displacement dispenser available from EFD Inc. of Providence, R.I. The ULTRA dispenser is typically used in the dispensing of small volumes of industrial adhesives. It utilizes a conventional syringe and a custom dispensing tip. The syringe plunger is actuated using an electrical stepper motor and an actuating fluid. Parker Hannifin Corporation of Cleveland, Ohio distributes a small volume liquid dispenser for drug discovery applications made by Aurora Instruments LLC of San Diego, Calif. The Parker/Aurora dispenser utilizes a piezo-electric dispensing mechanism. Ypsomed, Inc. of Switzerland produces a line of injection pens and automated injectors primarily for the self-injection of insulin or hormones by a patient. This product line includes simple disposable pens and electronically-controlled motorized injectors.

U.S. Pat. No. 6,290,690 discloses an ophthalmic system for injecting a viscous fluid (e.g. silicone oil) into the eye while simultaneously aspirating a second viscous fluid (e.g. perflourocarbon liquid) from the eye in a fluid/fluid exchange during surgery to repair a retinal detachment or tear. The system includes a conventional syringe with a plunger. One end of the syringe is fluidly coupled to a source of pneumatic pressure that provides a constant pneumatic pressure to actuate the plunger. The other end of the syringe is fluidly coupled to an infusion cannula via tubing to deliver the viscous fluid to be injected.

When a portable hand piece is used to inject a drug into the eye, it is important to provide a proper drug dosage. In one case, a phase transition compound or reverse gelation compound contains the drug. At room temperature, these compounds are in a solid state and have the consistency of wax. Because of their consistency, dosing an injector with these compounds can be difficult. The compounds can be brought to a more liquid state and drawn into the injector. However, this is a time consuming process that may not provide proper dosage. Drug pellets can be made by bringing the compounds to a more liquid state and sending the compounds through a drug molding apparatus. If the mold apparatus is properly designed, then a reliable dosage results.

SUMMARY OF THE INVENTION

In one embodiment consistent with the principles of the present invention, the present invention is a pellet loading apparatus. The apparatus has a pellet housing configured to receive and hold a plunger so that a cavity is formed by an interior surface of the pellet housing and the plunger. A pellet is located or formed in the cavity. A dispensing chamber housing is located in a disposable drug delivery device. The dispensing chamber housing is configured to couple with the pellet housing so that the plunger and the pellet can be loaded into the dispensing chamber housing.

In another embodiment consistent with the principles of the present invention, the present invention is a method of loading an ophthalmic injection device. A plunger is seated in a pellet housing to form a cavity bounded by an interior surface of the pellet housing and a top surface of the plunger. A substance is injected into the cavity to form a pellet. The top surface of the pellet housing is coupled to the bottom surface of a dispensing chamber housing. The plunger and the pellet are expelled into the dispensing chamber housing.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying figures, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying figures. Wherever possible, the same reference numbers are used throughout the figures to refer to the same or like parts.

Figure 1:
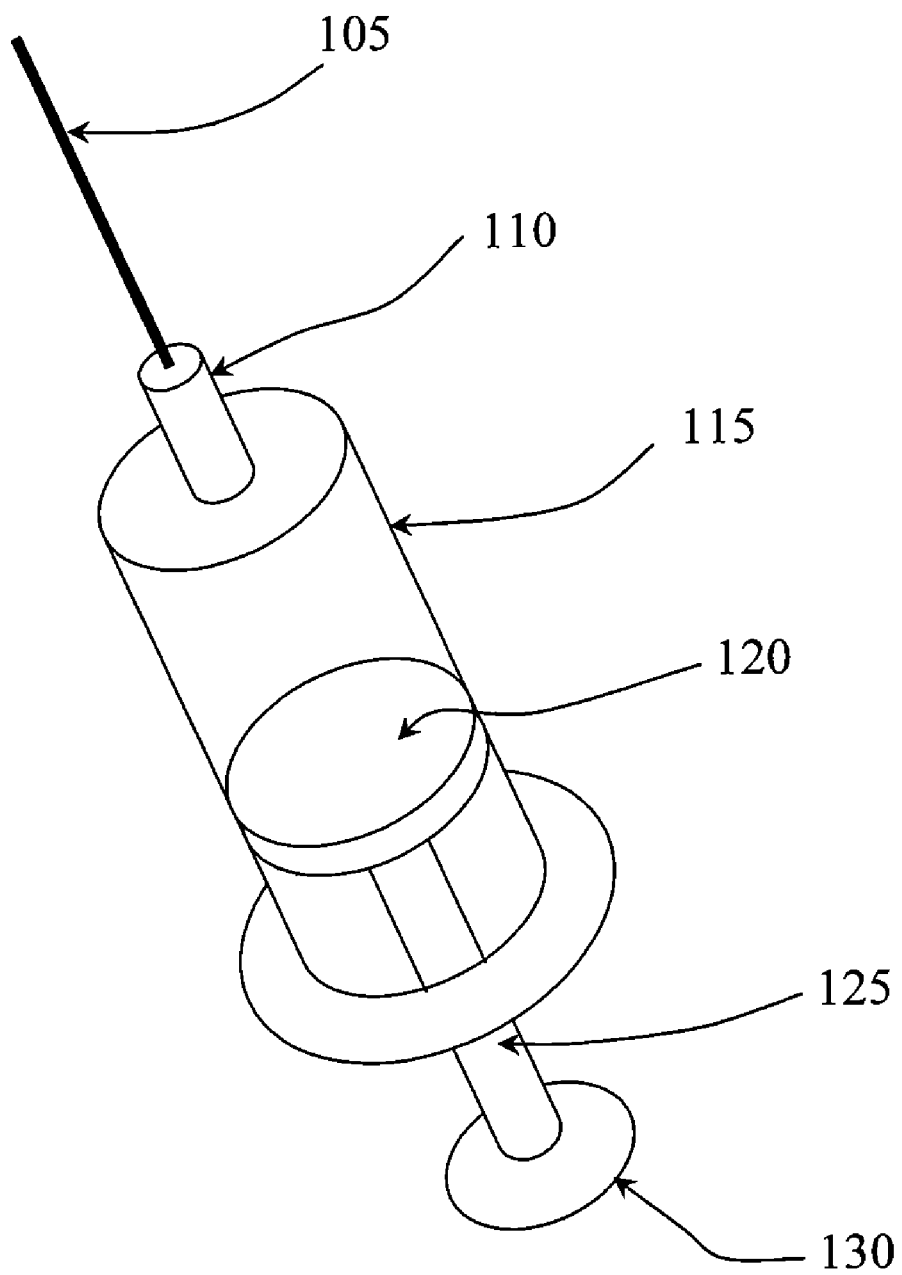
FIG. 1 is a perspective view of a prior art syringe.
Figure 2:
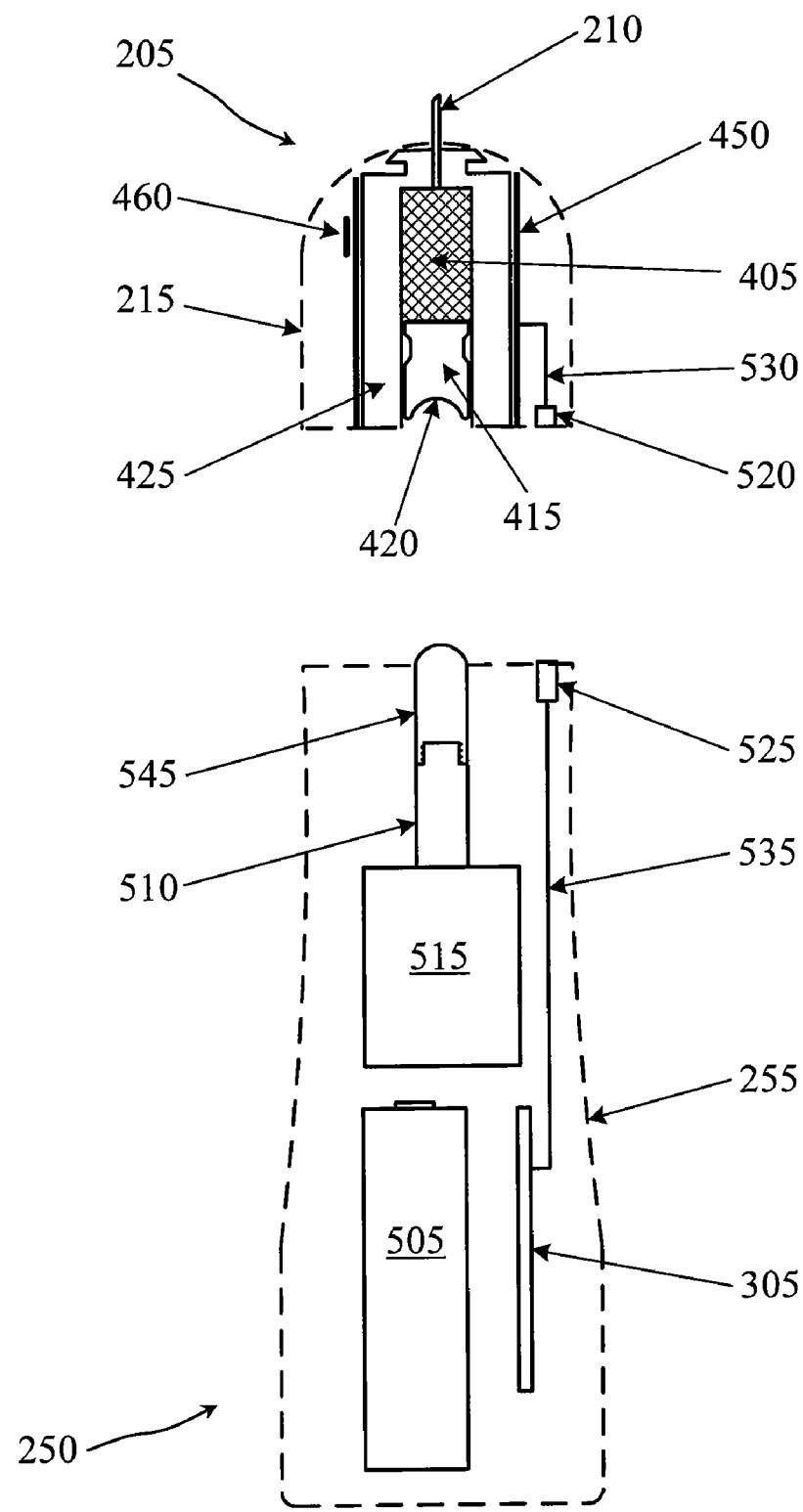
FIG. 2 is a cross section view of a disposable tip segment and a limited reuse assembly according to the principles of the present invention.

FIG. 2 is a cross section view of a disposable tip segment and a limited reuse assembly according to an embodiment of the present invention. FIG. 2 shows how tip segment 205 interfaces with limited reuse assembly 250. In the embodiment of FIG. 2, tip segment 205 includes plunger interface 420, plunger 415, dispensing chamber housing 425, tip segment housing 215, temperature control device 450, thermal sensor 460, needle 210, dispensing chamber 405, interface 530, and tip interface connector 520. Limited reuse assembly 250 includes mechanical linkage 545, actuator shaft 510, actuator 515, power source 505, controller 305, limited reuse assembly housing 255, interface 535, and limited reuse assembly interface connector 525.

In tip segment 205, plunger interface 420 is located on one end of plunger 415. The other end of plunger 415 forms one end of dispensing chamber 405. Plunger 415 is adapted to slide within dispensing chamber 405. An outer surface of plunger 415 is fluidly sealed to the inner surface of dispensing chamber housing 425. Dispensing chamber housing 425 surrounds the dispensing chamber 405. Typically, dispensing chamber housing 425 has a cylindrical shape. As such, dispensing chamber 405 also has a cylindrical shape.

Needle 210 is fluidly coupled to dispensing chamber 405. In such a case, a substance contained in dispensing chamber 405 can pass through needle 210 and into an eye. Temperature control device 450 at least partially surrounds dispensing chamber housing 425. In this case, temperature control device 450 is adapted to heat and/or cool dispensing chamber housing 425 and any substance contained in dispensing chamber 405. Interface 530 connects temperature control device 450 and thermal sensor 460 with tip interface connector 520.

The components of tip segment 205, including dispensing chamber housing 425, temperature control device 450, and plunger 415 are at least partially enclosed by tip segment housing 215. In one embodiment consistent with the principles of the present invention, plunger 415 is sealed to the interior surface of dispensing chamber housing 425. This seal prevents contamination of any substance contained in dispensing chamber 405. For medical purposes, such a seal is desirable. This seal can be located at any point on plunger 415 or dispensing chamber housing 425.

In limited reuse assembly 250, power source 505 provides power to actuator 515. An interface (not shown) between power source 505 and actuator 515 serves as a conduit for providing power to actuator 515. Actuator 515 is connected to actuator shaft 510. When actuator 515 is a stepper motor, actuator shaft 510 is integral with actuator 515. Mechanical linkage interface 545 is connected to actuator shaft 510. In this configuration, as actuator 515 moves actuator shaft 510 upward toward needle 210 mechanical linkage interface 545 also moves upward toward needle 210.

Controller 305 is connected via interface 535 to limited reuse assembly interface connector 525. Limited reuse assembly interface connector 525 is located on a top surface of limited reuse assembly housing 255 adjacent to mechanical linkage interface 545. In this manner, both limited reuse assembly interface connector 525 and mechanical linkage interface 545 are adapted to be connected with tip interface connector 520 and plunger interface 420 respectively.

Controller 305 and actuator 515 are connected by an interface (not shown). This interface (not shown) allows controller 305 to control the operation of actuator 515. In addition, an interface (not shown) between power source 505 and controller 305 allows controller 305 to control operation of power source of 310. In such a case, controller 305 may control the charging and the discharging of power source 505 when power source 505 is a rechargeable battery.

Controller 305 is typically an integrated circuit with power, input, and output pins capable of performing logic functions. In various embodiments, controller 305 is a targeted device controller. In such a case, controller 305 performs specific control functions targeted to a specific device or component, such as a temperature control device or a power supply. For example, a temperature control device controller has the basic functionality to control a temperature control device. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions. While depicted as one component, controller 305 may be made of many different components or integrated circuits.

Figure 5:
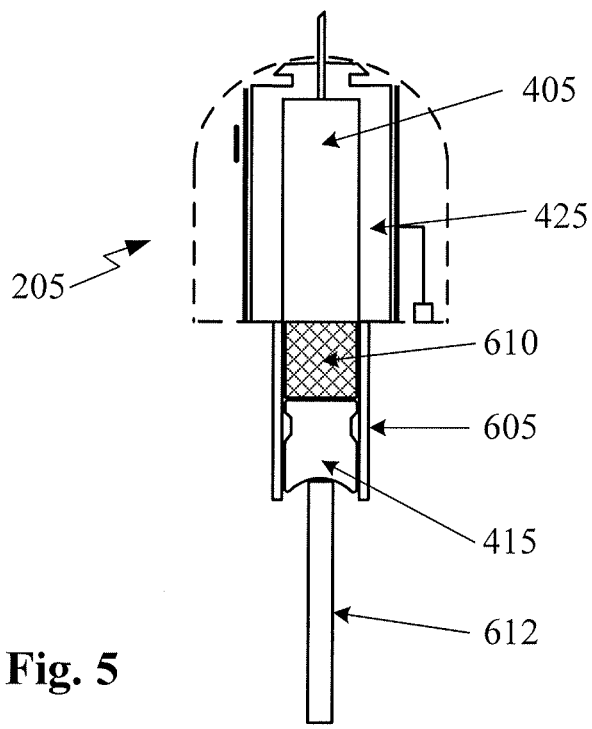
FIG. 5 is a cross section view of a drug pellet molding apparatus and a tip segment in a loading position according to the principles of the present invention.

Tip segment 205 is adapted to mate with or attach to limited reuse assembly 250 as previously described. In the embodiment of FIG. 5, plunger interface 420 located on a bottom surface of plunger 415 is adapted to mate with mechanical linkage interface 545 located near a top surface of limited reuse assembly housing 255. In addition, tip interface connector 520 is adapted to connect with limited reuse assembly interface connector 525. When tip segment 205 is connected to limited reuse assembly 250 in this manner, actuator 515 and actuator shaft 510 are adapted to drive plunger 415 upward toward needle 210. In addition, an interface is formed between controller 305 and temperature control device 450. A signal can pass from controller 305 to temperature control device 450 through interface 535, limited reuse assembly interface connector 525, tip interface connector 520, and interface 530.

In operation, when tip segment 205 is connected to limited reuse assembly 250, controller 305 controls the operation of actuator 515. Actuator 515 is actuated and actuator shaft 510 is moved upward toward needle 210. In turn, mechanical linkage interface 545, which is mated with plunger interface 420, moves plunger 415 upward toward needle 210. A substance located in dispensing chamber 405 is then expelled through needle 210.

In addition, controller 305 controls the operation of temperature control device 450. Temperature control device 450 is adapted to heat and/or cool dispensing chamber housing 425. Since dispensing chamber housing 425 is at least partially thermally conductive, heating or cooling dispensing chamber housing 425 heats or cools a substance located in dispensing chamber 405. Temperature information can be transferred from thermal sensor 460 to controller 305 via any of a number of different interface configurations. This temperature information can be used to control the operation of temperature control device 450. When temperature control device 450 is a heater, controller 305 controls the amount of current that is sent to temperature control device 450. The more current sent to temperature control device 450, the hotter it gets. In such a manner, controller 305 can use a feed back loop utilizing information from thermal sensor 460 to control the operation of temperature control device 450. Any suitable type of control algorithm, such as a proportional integral derivative (PID) algorithm, can be used to control the operation of temperature control device 450.

In various embodiments of the present invention, temperature control device 450 heats a phase transition compound that is located in dispensing chamber 405. This phase transition compound carries a drug that is to be injected into the eye. A phase transition compound is in a solid or semi-solid state at lower temperatures and in a more liquid state at higher temperatures. Such a substance can be heated by temperature control device 450 to a more liquid state and injected into the eye where it forms a bolus that erodes over time. Likewise, a reverse gelation compound may be used. A reverse gelation compound is in a solid or semi-solid state at higher temperatures and in a more liquid state at lower temperatures. Such a compound can be cooled by temperature control device 450 to a more liquid state and injected into the eye where it forms a bolus that erodes over time. As such, temperature control device 450 may be a device that heats a substance in dispensing chamber 405 or a device that cools a substance in dispensing chamber 405 (or a combination of both). After being delivered into the eye, a phase transition compound or reverse gelation compound erodes over time providing a quantity of drug over an extended period of time. Using a phase transition compound or reverse gelation compound provides better drug dosage with fewer injections.

Figure 3:
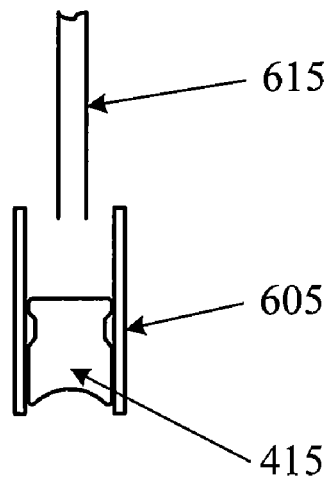
FIG. 3 is a cross section view of a drug pellet molding apparatus according to the principles of the present invention.

FIG. 3 is a cross section view of a drug pellet molding apparatus according to the principles of the present invention. In FIG. 3, pellet housing 605 surrounds plunger 415. A dispensing tube 615 is configured to fill the cavity above plunger 415 in pellet housing 605. In one embodiment of the present invention, pellet housing 605 is generally cylindrical in shape so that plunger 415 (which is also generally cylindrical in shape) fits tightly within pellet housing 605. Plunger 415 fits within pellet housing 605 tightly so that a leak resistant or leak proof seal is formed. In this manner, a substance placed in the cavity bounded by the interior surface of pellet housing 605 and the top of plunger 415 does not leak out toward the bottom of plunger 415. When plunger 415 is located in pellet housing 605, a cavity is formed above plunger 415. This cavity is filled with a substance (e.g. drug-compound mixture) by dispensing tube 615 or other mechanism.

In another embodiment consistent with the principles of the present invention, pellet housing 605 may also be heated. When the substance cast into pellet housing 605 on top of plunger 415 is a phase transition compound, it may be desirable to heat pellet housing 605 so that the compound remains in a relatively liquid state when it is located in pellet housing 605. In this manner, pellet housing 605 can be made from any of a number of different thermally conductive materials that are suitable for contact with a pharmaceutical (e.g. stainless steel or glass).

Figure 6:
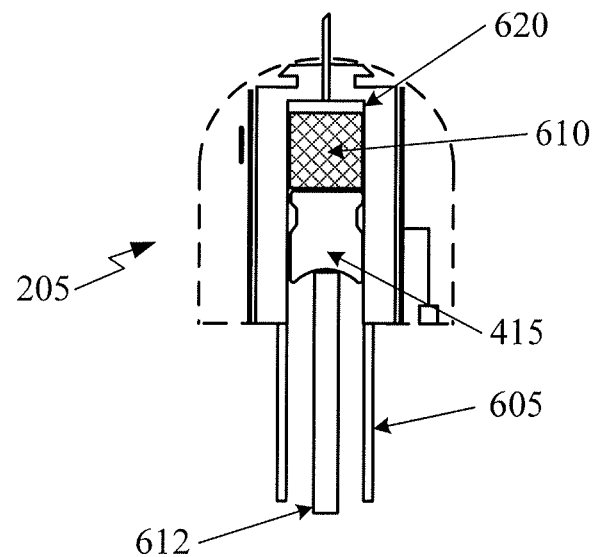
FIG. 6 is a cross section view of a drug pellet molding apparatus and a tip segment in a loading position according to the principles of the present invention.

In another embodiment of the present invention, pellet housing 605 is not heated. Instead, when plunger 415 is moved into dispensing chamber housing 425 (as shown in FIGS. 5 & 6), friction between pellet 610 and the interior surface of pellet housing 605 (and the interior surface of dispensing chamber housing 425 as well) can assist in the removal of air entrapped in pellet 610. As more fully explained with reference to FIG. 6, it is desirable to have an air gap between the top of pellet 610 and the needle. This frictional force between pellet 610 and the interior surface of pellet housing 605 (and the interior surface of dispensing chamber housing 425 as well) can be beneficial for creating a precise air gap 620.

Figure 4:
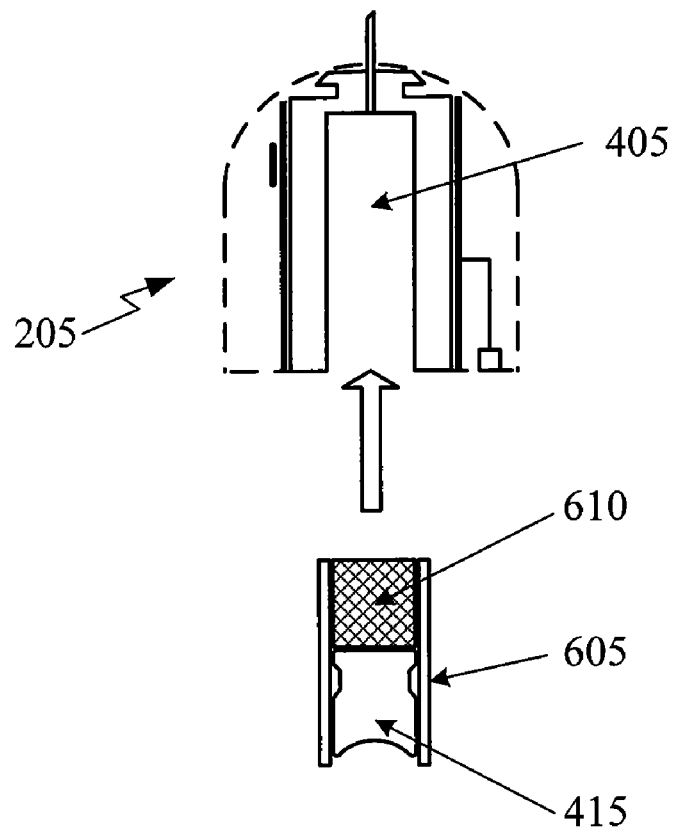
FIG. 4 is a cross section view of a drug pellet molding apparatus and a tip segment according to the principles of the present invention.

FIG. 4 is a cross section view of a drug pellet molding apparatus and a tip segment according to the principles of the present invention. FIG. 4 shows one step in the loading process of pellet 610 into dispensing chamber 405. In this step, pellet 610 has been cast into pellet housing 605 on top of plunger 415. In this manner, a substance (e.g. a phase transition compound/drug mixture) was heated to a more liquid state and injected into the cavity formed by the interior surface of pellet housing 605 and the top surface of plunger 415. In the position shown in FIG. 4, pellet housing 605 may or may not be heated depending on the desired insertion results. If pellet housing 605 is heated, (and pellet 610 is in a more liquid state), then when pellet housing 605 is in the position shown in FIG. 5, pellet 610 may be more easily inserted into dispensing chamber housing 425. If pellet housing 605 is not heated, then more friction is present between the interior surface of pellet housing 605 and pellet 610. While pellet 610 is generally described to be solid, it may also be in a semi-liquid or liquid state during the insertion procedure.

FIG. 5 is a cross section view of a drug pellet molding apparatus and a tip segment in a loading position according to the principles of the present invention. In the position shown in FIG. 5, pellet 610 is ready to be inserted (along with plunger 415) into dispensing chamber 405. In this position, pellet housing 605 may or may not be heated (as previously mentioned) and dispensing chamber housing may or may not be heated. An insertion rod 612 pushes plunger 415 and pellet 610 into dispensing chamber 405 as shown in FIG. 6.

Further, the top surface of pellet housing 605 that contacts the bottom surface of dispensing chamber housing 425 may have a physical structure that allows the housing 405 to couple with the dispensing chamber housing 425. In other words, a groove (or other physical feature—such as a hole) may be present on the bottom surface of dispensing chamber housing 425. A complementary ridge (or other physical feature such as a pin) may be present on the top surface of pellet housing 605 so that pellet housing 605 mates with dispensing chamber housing 425. This helps to secure temporarily pellet housing 605 to dispensing chamber housing 425 so that pellet 610 can be inserted into dispensing chamber 405.

FIG. 6 is a cross section view of a drug pellet molding apparatus and a tip segment in a loading position according to the principles of the present invention. In FIG. 6, plunger 415 and pellet 610 have been loaded into dispensing chamber 405. In this configuration, an air gap 620 is present in dispensing chamber 405. In other words, air is purposely trapped in dispensing chamber along with the pellet. This entrapped air or air gap 620 provides advantages in the drug delivery process.

When the pellet 610 is a drug suspended in a phase transition compound, the pellet is heated as dispensing chamber housing 425 is heated. Needle 210 is also heated. The pellet 610 expands as it is heated. As the pellet expands, the air in the air gap (605 or 615 as the case may be) escapes through needle 210. The pellet 610 expands to substantially fill the dispensing chamber or volume enclosed by dispensing chamber housing 425 and plunger 415. A small amount of the pellet may also expand into needle 210. However, it is important to keep air in the protruding portion of needle 210 to prevent the drug/phase transition compound mixture from solidifying in needle 210 and blocking it during injection. Since needle 210 is cooler than dispensing chamber housing 425 and pellet 610, if any significant amount of the drug/phase transition compound mixture enters the protruding portion of needle 210, it rapidly cools and solidifies, blocking the needle 210. Accordingly, applicants have made the discovery that keeping air in needle 210 and injecting that air into the eye along with the pellet 610 is beneficial for a controlled injection.

When the pellet 610 and the dispensing chamber bounded by the dispensing chamber housing 425 are both cylindrical, the air gap is calculated by using the formula for the volume of a cylinder. The volume of the dispensing chamber is denoted by $V_{DC}$, the volume of the pellet at a first temperature is denoted by $V_{P1}$, and the volume of the pellet at a second temperature is denoted by $V_{P2}$:

$$V_{DC} = \pi R_{DC}^2 \cdot H_{DC}$$

$$V_{P1} = \pi R_{P1}^2 \cdot H_{P1}$$

$$V_{P2} = \pi R_{P2}^2 \cdot H_{P2}$$

where $R_{DC}$ and $H_{DC}$ are the radius and height, respectively, of the dispensing chamber, $R_{P1}$ and $H_{P1}$ are the radius and height, respectively, of the cylindrical pellet at a first temperature, and $R_{P2}$ and $H_{P2}$ are the radius and height, respectively, of the cylindrical pellet at a second temperature. In this example, the volume of the dispensing chamber is known and does not change. Since the pellet is made of a phase transition compound, its volume changes as a function of temperature. When the pellet is made of a phase transition compound/drug mixture (Precirol/pharmaceutical), the first temperature is 20 to 23 degrees Celsius, and the second temperature is 75 degrees Celsius, it was found that $V_{T2}=1.2 \cdot V_{T1}$ (where 1.2 is an example value of a thermal coefficient of expansion at 75 degrees Celsius from 23 degrees Celsius). In other words, the volume of the pellet increases by twenty percent when it is heated to 75 degrees Celsius from room temperature. The air gap is then calculated by taking the difference between $V_{T2}$ and $V_{T1}$ (i.e. $V_{T2}-V_{T1}$=volume of air gap). This volume of air gap can then be maintained in the dispensing chamber by forming a pellet with the volume, $V_{T1}$. A pellet with this volume (and any shape) can then be placed in the dispensing chamber on top of the plunger.

From the above, it may be appreciated that the present invention provides an improved system for preparing drug dosage. The present invention provides an apparatus that is designed to reliably make pellets of a consistent quality. This apparatus is configured to form pellets from a drug/compound mixture that is solid at room temperature but liquid at other temperatures. The finished pellets are of the proper size to produce a reliable dosage when injected into the eye.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A pellet loading apparatus comprising:
   a plunger movably coupled to an insertion rod, the plunger being cylindrical in shape and having a first diameter;
   a pellet housing having an interior surface that defines a cylindrical cavity with a second diameter configured to receive and hold the plunger, the plunger movable within the pellet housing by application of force from the insertion rod;
   a pellet located in the cavity; and
   a dispensing chamber housing having an interior surface that defines a cylindrical cavity with a third diameter and located in a disposable tip segment, the dispensing chamber housing configured to abut the pellet housing and to be removable from the pellet housing so that the plunger and the pellet can be loaded into the dispensing chamber housing, such that the plunger is fully retained-in the dispensing chamber housing when the pellet housing is decoupled from the dispensing chamber housing; wherein the first, second, and third diameters are the same.

2. The apparatus of claim 1 further comprising:
   a needle fluidly coupled to the dispensing chamber housing.

3. The apparatus of claim 1 further comprising:
   a temperature control device at least partially surrounding the dispensing chamber housing.

4. The apparatus of claim 1 wherein the pellet housing is heated.

5. The apparatus of claim 1 further comprising:
   an injection tube for injecting the pellet into the cavity.

* * * * *